(12) United States Patent
Hua et al.

(10) Patent No.: US 9,708,617 B2
(45) Date of Patent: Jul. 18, 2017

(54) METHOD OF ANAEROBIC TISSUE-TARGETED GENE EXPRESSION INITIATED BY ALCOHOL DEHYDROGENASE PROMOTER AND THE APPLICATION THEREOF

(75) Inventors: Zichun Hua, Jiangsu (CN); Jianxiang Chen, Jiangsu (CN); Dongping Wei, Jiangsu (CN); Hongqin Zhuang, Jiangsu (CN)

(73) Assignee: NANJING UNIVERSITY (CN)

( * ) Notice: Subject to any disclaimer, the term of this patent is extended or adjusted under 35 U.S.C. 154(b) by 0 days.

(21) Appl. No.: 14/119,452

(22) PCT Filed: May 13, 2011

(86) PCT No.: PCT/CN2011/000839
§ 371 (c)(1),
(2), (4) Date: Nov. 22, 2013

(87) PCT Pub. No.: WO2012/139254
PCT Pub. Date: Oct. 18, 2012

(65) Prior Publication Data
US 2014/0093885 A1 Apr. 3, 2014

(30) Foreign Application Priority Data
Apr. 12, 2011 (CN) .......................... 2011 1 0094337

(51) Int. Cl.
*C12N 15/74* (2006.01)
*C12N 15/70* (2006.01)
(52) U.S. Cl.
CPC ............. *C12N 15/74* (2013.01); *C12N 15/70* (2013.01)

(58) Field of Classification Search
None
See application file for complete search history.

(56) References Cited

U.S. PATENT DOCUMENTS

2003/0113293 A1* 6/2003 Bermudes .............. A61K 48/00
424/93.2

OTHER PUBLICATIONS

Chen et al., Mol Cell Proteomics, 2011, pp. 1-44.*
Chen et al. Molecular and Cellular Proteomics, 2011, vol. 10.6, pp. 1-11.*
Dailly et al., Microbios, 2000, vol. 103, pp. 179-196.*

* cited by examiner

*Primary Examiner* — Mindy G Brown
(74) *Attorney, Agent, or Firm* — Schmeiser, Olsen & Watts, LLP

(57) ABSTRACT

A proteomic screening method for anaerobic-specific and expression-effective promoter, and a method of specially delivering and selectively stably expressing target gene in anaerobic tissue by an alcohol dehydrogenase promoter and uses thereof. The latter comprises an anaerobically-induced alcohol dehydrogenase promoter which is used as target gene promoter, anaerobic target bacteria and low copy number plasmid. Therefore, the target gene can be specially and highly expressed under hypoxia condition in vivo or in vitro. The selective gene expression which is driven by the alcohol dehydrogenase promoter in anaerobic tissue can be used as gene therapy method to treat anaerobic tissue disease including tumor, or to prepare anti-tumor drug.

9 Claims, 11 Drawing Sheets

Figure 1A:
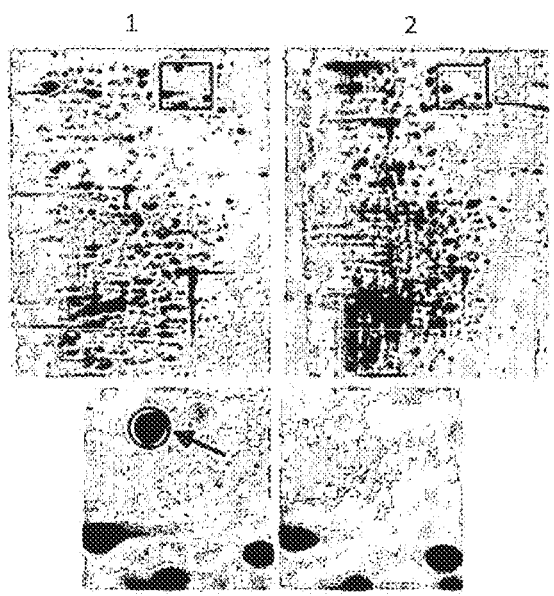

FIG. 4C
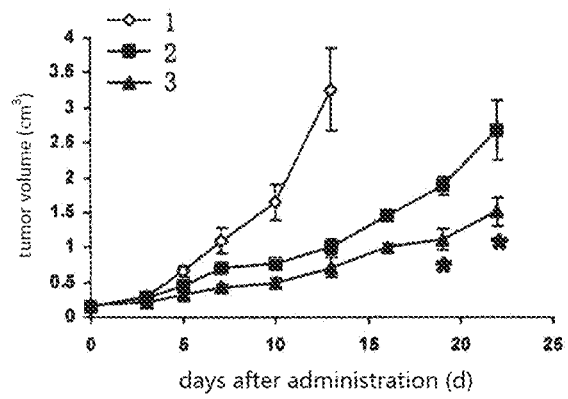
FIG. 4D
FIG. 4E
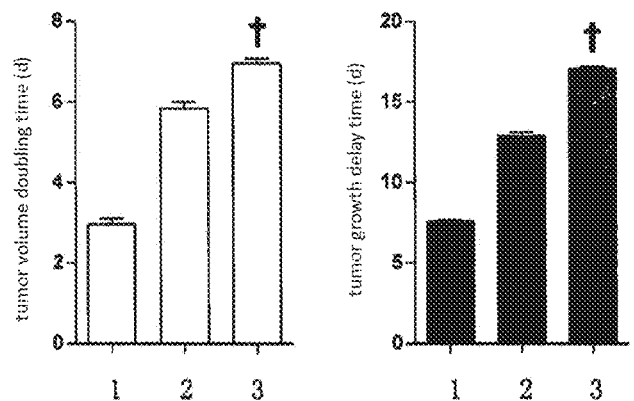

METHOD OF ANAEROBIC TISSUE-TARGETED GENE EXPRESSION INITIATED BY ALCOHOL DEHYDROGENASE PROMOTER AND THE APPLICATION THEREOF

CROSS-REFERENCE TO RELATED APPLICATIONS

This application claims priority to PCT Application No. PCT/CN2011/000839, having a filing date of May 13, 2011, the entire contents of which are hereby incorporated by reference.

FIELD OF TECHNOLOGY

The following relates to gene engineering and biotechnology, specifically to the proteomic technique of screening an anaerobic-specific promoter, the method to realize anaerobic tissue-targeted delivery and stable, selective expression of the therapeutic gene initiated by the anaerobic-specific alcohol dehydrogenase promoter screened out through the said proteomic technique, and the practical application of these methods.

BACKGROUND

The antitumor gene therapy presents a vast application prospect in view of the fact that it can fundamentally correct the abnormal gene expression and the corresponding imbalance appeared during the genesis and growth of tumors. However, currently there exists a few severe challenges in this field. For example, under the circumstances of systematic medication, how to control the delivered therapeutic gene merely within the solid tumor. Or, how to realize the high-level, high-specific expression of the therapeutic gene in the whole tumor while no expression at all in other normal tissues so that the side effects can be eliminated or reduced. Such technical challenges restrict the practical application of the gene therapy in treatment of solid tumors, as safety and efficacy are extremely important factors that have to be taken into consideration in the research and development of gene therapeutic vectors for tumor treatment. Many solid tumors, including most of primary tumors such as mammary cancer and melanoma, have characteristic anoxic or necrotic areas [Patyar S, et. al. 2010, Journal of Biomedical Science 17:21; Li X, et, al. 2003, Cancer Gene Therapy 10:105-111]. The partial pressure of oxygen in tumors, as tissue-oxygen analysis of the tumor patients has shown, is 10-30 mmHg while the partial pressure of oxygen in other normal tissues is 24-66 mmHg. In addition, the tumor cells in the anoxic or necrotic areas are not sensitive to radiotherapy and chemotherapy, which means that the traditional radiotherapy and chemotherapy are unable to kill the tumor cells completely. This consequently lowers down the tumor patients' tolerance to these traditional therapeutic methods, and results in high frequency of recurrence and metastasis of the tumors.

In view of these facts, the development of delivery systems and expression patterns of the therapeutic gene targeting to the anoxic or necrotic areas of tumors has recently become a hot topic in the field of gene therapy of solid tumors. Some anaerobic or facultative anaerobic bacteria, such as *Salmonella typhimurium, Clostridium* and bifidobacterium, can selectively colonize in the anoxic areas of tumors after a systematic infection process, [Patyar S, et, al. 2010, Journal of Biomedical Science 17:21; Li X, et, al. 2003, Cancer Gene Therapy 10:105-111]; and they can also stimulate the immuno-antitumor activities of the body. [Lee C H, et, al. 2009, Journal of Immunotherapy 32:376-388; Chen G, et, al. 2009, Cancer Science 100:2437-2443; Avogadri F, et, al. 2005, Cancer Research 65:3920-3927; Liu T, et, al. 2010, Cancer Gene Therapy 17:97-108; Eisenstein T K, et, al. 2001, Microbes and Infection 3:1223-1231]. However, the proliferation of bacteria cannot stop the growth of malignant tumors alone. In order to enhance bacteria's antitumor performance, researchers tried to introduce *Salmonella* bearing specific gene or protein to the tumor tissue while keeping other normal tissues unaffected. Recently, a series of progressions have been achieved by researchers in adopting *Salmonella typhimurium* as the tumor-targeted vector in gene therapy. A variety of attempts have been made to manipulate the expression of the antitumor gene. Prokaryotic promoters such as arabinose-induced promoter and outer membrane protein C (ompC) promoter, eukaryotic constitutive promoters such as β-actin promoter and the radiation-induced promoter found in eukaryotic cells, have all been put into experiments. They all present significant antitumor effect [Ganai S et, al. 2009, British Journal of Cancer 101:1683-1691; Brader P, et, al, 2008, Clinical Cancer Research 14:2295-2302; Weth R, et, al. 2001, Cancer Gene Therapy 8:599-611; Loessner H, et, al. 2007, Cellular Microbiology 9:1529-1537; Nguyen V H, et, al. 2010, Cancer Research 70:18-23; Loeffler M, et, al. 2007, Proceedings of the National Academy of Sciences of the United States of America 104:12879-12883; Loeffler M, et, al. 2008, Journal of the National Cancer Institute 100:1113-1116; Loeffler M et, al. 2008, Cancer Gene Therapy 15:787-794; Loeffler M, et, al. 2009, Cancer Immunology Immunotherapy 58:769-775; Lee C H, et, al. 2004, Journal of Gene Medicine 6:1382-1393; Lee C H, et, al. 2005, Cancer Gene Therapy 12:175-184; King I, et, al. 2002, Human Gene Therapy 13:1225-1233; Li Y H, et, al. 2001, International Journal of Cancer 94:438-443]. However, problems still exist in the above mentioned expression systems. For example, some researches showed that, when the attenuated strain of a certain bacterium was adopted to treat tumor-bearing mice, not only did it aggregate in the tumor but it also colonized in normal tissues [Clairmont C, et, al. 2000, Journal of Infectious Diseases 181:1996-2002], which resulted in undesired expression of the target gene in normal tissues and consequently in vivo toxicity; When recombinant *Salmonella* was adopted to carry constitutive promoters and to initiate the downstream target gene, the said multiple-organ distribution pattern may engender certain negative effects (for example, toxic effect) and therefore undermine the specificity of gene therapy [King I, et, al 2002, Human Gene Therapy 13:1225-1233; Low K B, et, al. 1999, Nature Biotechnology 17:37-41]; in addition, the high level of heterologous protein expressed through the strong promoter probably leads to intracellular toxicity, which will cause heavy loss of plasmid during the infection process [Hautefort I, et, al. 2003, Applied and Environmental Microbiology 69: 7480-7491]. Other problems include poor in vivo stability of the plasmid vector expressed by the gene and the low level of in vivo expression of the target gene (i.e. protein expression could not be detected by conventional methods such as protein electrophoresis and western blot) [Weth R, et, al. 2001, Cancer Gene Therapy 8:599-611; Li Y H, et, al. 2001, International Juornal of Cancer 94:438-443; Pawelek J M, et, al. 1997, Cancer Research 57:4537-4544; Liu S C, et, al. 2002, Gene Therapy 9:291-306; Nemunaitis J, et, al. 2003, Cancer Gene Therapy 10:737-744].

SUMMARY

To solve these problems, which means to realize high-specific, high-level expression of the target gene induced by tumor-targeted bacteria in the tumor tissue, and to maintain high in vivo stability of the plasmid so that the gene therapy can present not only excellent and sustained therapeutic effect but also less toxic and side effects, is of great urgency to be overcome in the field of tumor-targeted bacteria-induced gene therapy.

A first aspect relates to a method of preparing promoters for anaerobic-specific expression through proteomic screening. The alcohol dehydrogenase promoter and the anaerobic-targeted bacteria obtained through this method realize high-level, selective expression of the therapeutic gene in the anaerobic tissue and desirable in vivo stability of the plasmid, which therefore guarantees not only excellent and sustained therapeutic effect but also fewer toxic and side effects.

The technical solution is to screen out the anaerobic-specific gene and its promoter through the proteomic technique. The said promoter of the target gene is anaerobic-specific, which means it can initiate the expression of the target gene under hypoxic or anaerobic conditions.

The proteomic technique adopted for screening anaerobic-specific gene and its promoter is further utilized to obtain alcohol dehydrogenase promoter padhE from *Salmonella*. The said pdahE promoter is highly conservative in prokaryotic bacteria. The DNA sequence of the said promoter pdahE has 100% identity with the DNA sequence of such serotypes of *Salmonella enterica* as *S. typhimurium* 4/74, T000240, SL1344, 14028S, D23580, LT2, *S. heidelberg* SL476, etc.; 99% identity with the DNA sequence of such serotypes of *Salmonella enterica* as *S. enteritidis* P125109, *S. dublin* CT_02021853, *S. gallinarum* 287/91, *S. newport* SL254, and *S. paratyphi* SPB7, etc.; 98% identity with the DNA sequence of such serotypes of *Salmonella enterica* as *S. agona* SL483, *S. schwarzengrund* CVM19633, *S. choleraesuis* SC-B67, *S. paratyphi*-C RKS4594, *S. typhi* Ty2, *S. weltevreden* 2007-60-3289-1, *S. paratyphi*-A AKU_12601 and *S. paratyphi*-A ATCC 9150, etc; 98% identity with the DNA sequence of *S. typhi* CT18; 93% identity with the DNA sequence of such serotypes of *Salmonella enterica* as *S. arizona* 62:z4 and z23:--; 88% identity with the DNA sequence of *Klebsiella variicola* At-22 and such serotypes of *Klebsiella pneumoniae* as NTUH-K2044, 243, MGF78578; 81% identity with the DNA sequence of *Citrobacter koseri* ATCC BAA-895; 80% identity with the DNA sequence of *Citrobacter rodentium* ICC168; 79% identity with the DNA sequence of *Shigella dysenteriae* Sd197; 77% identity with the DNA sequence of such serotypes of *Escherichia coli* as SMs-3-5, 536, 083: H1, UM146, IHE3034, 026:H11, LF82, S88, APEC 01, UT189, KO11, W, BL21(DE3), ETEC H10407, ABU83972, 0111: H-strain, 0103: H2, *Escherichia coli* B REL606, BL21-Gold(DE3)pLysS AG', UMN026, ED1a, IAI39, IAII, 55989, SE11, ATCC8739, E24377A, HS, CFT073, 042, DH1 (ME8569), DH1, 0157:H7, BW2952, 0127:H6E2348/69, 0157: H7 EC4115, K12 DHI0B, K12 W3110, K12 MG1655, 0157:H7-0157:H7EDL933, 0155:H7-CB9615 and SE15; 77% identity with the DNA sequence of *Escherichia Fergusonii* ATCC 35469; 77% identity with the DNA sequence of such serotypes of *Shigella dysenteriae* as 2002017, 2a and 2a 2457T; 77% identity with the DNA sequence of *Shigella sonnei* SS046, *Shigella boydit* CDC3083-94, *Shigella flexneri* 5-8401 and *Shigella boydit* Sb227; 76% identity with the DNA sequence of *Escherichia coli* 0157; and 75% identity with the DNA sequence of enterobacter cloacae SCF1. As shown above, the said promoter padhE is highly conservative in bacteria, and all padhE promoters made from prokaryotic bacteria can be used to initiate anaerobic-specific expression of the bacteria-induced target gene.

In addition, the core sequence of the promoter padhE must contain the fragment at least 1200 bp upstream of the adhE gene so that the said promoter can initiate the selective expression under hypoxic or anaerobic conditions. Within the said sequence, the sequences at 500 bp and 1000 bp upstream of the adhE gene can also realize high-level expression of the reporter gene, however, both of them are not anaerobic-specific; on the contrary, the DNA sequence at 1000 bp-1200 bp upstream of the adhE gene can guarantee high-level anaerobic expression of the said promoter. As to the sequence extending further than 1200 bp upstream of the adhE gene, it certainly has selective expression property due to the fact that it contains the DNA sequence at 1200 bp upstream of the adhE gene; the region around 1200 bp contains a part of ychE gene that is further upstream of the adhE gene, the said ychE gene is of assistance to the promoter padhE.

A cloning method for preparing secretory expression plasmid of the padhE-initiated target gene. Firstly, cloning the padhE-initiated therapeutic gene into the plasmid that contains the prokaryotic replicon so that the expression of the target gene in anaerobic-targeted bacteria can be achieved under hypoxic or anaerobic conditions.

Specifically, amplifying the gene fragment obtained through fusion of SPA secretory signal peptide and the target gene by means of PCR reaction, ligating the said gene fragment with the promoter adhE through overlapping PCR reaction; after being cleaved by restriction endonucleases, the ligated product is combined with *Escherichia coli* plasmid that has been digested by enzymes, and then transforming into *E. coli* TOP 10 competent cells; after the clone cultureand screening process, the secretory expression plasmid of the adhE-initiated target gene is therefore obtained; and it enables the target gene to express in the anaerobic-targeted bacteria under hypoxic or anaerobic conditions.

A cloning method for realizing stable existence of the said expression plasmid of the padh-initiated target gene in the anaerobic-targeted bacteria. Cloning the promoter padhE and the target gene under its control into the low-copy plasmid so that the stable in vivo existence of the promoter padhE and the target gene under its control can be realized in the anaerobic-targeted bacteria. The said low-copy plasmid can aggregate in large quantity in the tumor tissue and can reach stable, specific expression in the tumor tissue as well, regardless of time change.

Specifically, amplifying the gene fragment obtained through the fusion of SPA secretory signal peptide and the target gene by means of PCR reaction, splicing the said gene fragment with the promoter adhE through overlapping PCR reaction; after being cleaved by restriction endonucleases, the spliced product is combined with *E. coli* pBR332 plasmid that has been cleaved by enzymes, and then transforming the product into TOP 10 competent cells; after the clone culture and screening process, the secretory expression plasmid of the adhE-initiated target gene is therefore obtained. Transforming the said expression plasmid into attenuated *S. typhimurium* VNP20009 and delivering the product to tumor-bearing animal models through oral, intravenous or abdominal administration; the said low-copy plasmid-containing attenuated *S. typhimurium* VNP20009 can aggregate in large quantity in the tumor tissue, and can reach stable, specific expression in the tumor tissue, regardless of time change.

A method for preparing an expression strain of bacteria modified by the padhE-initiated therapeutic gene, which can integrate the plasmid vector of the padh-initiated target gene into the anaerobic-targeted bacteria.

A method for constructing a strain of *Salmonella* that integrates the target gene at a certain site of its chromosome and accordingly ensures the stable expression of the target gene. Amplifying the target gene through PCR reaction, ligating the said gene fragment with the padhE-target gene through overlapping PCR reaction; meanwhile, obtaining MSB gene fragment from the *Salmonella* genome amplified by PCR primers MSB-1 and MSB-2; ligating the gene fragment so obtained with padh-target gene through overlapping PCR reaction again, cloning the product into the pDS132 vector, and then transforming the product into TOP10 competent cells; after the clone culture and screening process, the clone so obtained is the suicide plasmid of the padhE-containing target gene. Transforming the suicide plasmid of the padhE-target gene into attenuated *S. typhimurium* VNP20009; and by means of resistance screening, homologously integrating the padhE-target gene with MSB gene at the specific chromosome site of the said strain of bacteria.

Specifically, a method for constructing a strain of *Salmonella* that integrates the target gene at a certain site of its chromosome and accordingly ensures the stable expression of GFP. Obtaining GFP gene fragment from pEGFP plasmid amplified by primers GFP-1 and GFP-2; ligating the gene fragment so obtained with the padh fragment through overlapping PCR reaction; and then obtaining MSB fragment from the *Salmonella* genome amplified by primers MSB-1 and MSB-2; the fragment so obtained is homologous recombinant. Amplifying the said fragment again with primers MSB-1 an MSB-2, cleaving the PCR product with Hind III and Sal I; combining the fragment so obtained with pDS132 vector that has also been cleaved by Hind III and Sal I; transforming the product into TOP 10 competent cells; after the clone culture and screening process, the clone so obtained is the suicide plasmid of the adhE-containing GFP. Transforming the attenuated *S. typhimurium* VNP20009 with the suicide plasmid of the padhE-containing target gene, and by means of resistance screening, the padhE-target gene is homologously integrated into MSB gene at the specific chromosome site of the said strain of bacteria.

```
The primer of GFP-I is:
5'-TGCTGCAAATGCTATGGTGAGCAAGGCGA-3';

the primer of GFP-II is:
5'-ATACTGCAGTTACTTGTACAGCTCGTCCA-3';

the primer of MSB-I is:
5'-GCGTCTAGAGTGAGCAGATCGTCCATTG-3';

the primer of MSB-II is:
5'-GAGCTGCAGCGTTACATGCACTTGCGTA-3'.
```

A method for delivering the low-toxic expression strain containing the padhE-initiated therapeutic gene into the body. The oral administration can successfully deliver the strain modified by the padhE-initiated target gene into the body and can realize targeted aggregation of the strain in the anaerobic tissue; the toxic and side effects presented in this method is much lower than those in the conventional methods.

A method for targeted delivery and selective expression of the anaerobic-targeted bacteria containing the padh-initated target gene in the anaerobic tissue. Delivering the said anaerobic-targeted bacteria containing the padhE-initiated target gene into the body through abdominal injection, intravenous injection or oral administration; all the routes can realize high-level expression of the target gene in the anaerobic tissue and no expression of the target gene in other normal tissues.

The said method for targeted delivery and stable, selective expression of the padh-initiated target gene in the anaerobic tissue is adopted to prepare anaerobic tissue-targeted medicine and medicine for diseases causing anaerobic tissues.

The said method for targeted delivery and stable, selective expression of the padh-initiated target gene in the anaerobic tumor tissue is adopted to prepare anaerobic tumor-targeted medicine and selective, anti-tumor medicine.

Specifically, when the attenuated *Salmonella* NVP 20009 bearing the padhE-initiated Endostatin gene is adopted to treat the Lewis lung cancer models in mice, both attenuated *Salmonella* VNPpadEEnd and attenuated *Salmonella* VNP can significantly slow down the growth of the tumor. 12-18 days after inoculation, the volume of the tumor models treated by attenuated *Salmonella* VNPpadhEEnd is much smaller than that treated by attenuated *Salmonella* VNP. Further analysis of the tumor volume doubling time shows that the tumor volume doubling time of the control group is 3.46 days, attenuated *Salmonella* VNP group 4.44 days, and attenuated *Salmonella* VNPpadhEEnd group 5.21 days. In respect of the tumor growth delay, both attenuated *Salmonella* VNP (8.45 days) and attenuated *Salmonella* VNPpadhEEnd (11.43 days) show significant improvement in comparison with the control group (11.43 days). When adopted in the treatment of melanoma, attenuated *Salmonella* VNPpadhEEnd can significantly inhibit the growth of melanoma in comparison with the attenuated *Salmonella* VNP group and the control group. The tumor volume doubling time of the attenuated *Salmonella* VNPpadhEEnd group is 6.96 days, significantly longer than that of the attenuated *Salmonella* VNP group (5.86 days) and the control group (2.96 days). Meanwhile, the tumor growth delay time of the attenuated *Salmonella* VNPpadhEEnd group increases significantly, reaching 17.07 days in average, while the tumor growth delay time of the attenuated *Salmonella* VNP group and the control group is 12.90 days and 7.56 days respectively. In the case of lung cancer models, the medium survival time of the mice in the attenuated *Salmonella* VNPpadhEEnd group is 49.0 days, significantly longer than that in the control group (18.0 days) and the attenuated *Salmonella* VNP group (25.92 days); the Kaplan-Meier survival analysis shows that the treatment with attenuated *Salmonella* VNPpadhEEnd can significantly improve survival rate of mice; the 30-day survival rate of mice in the attenuated *Salmonella* VNPpadhEEnd group and the attenuated *Salmonella* VNP group is 86% and 71% respectively. In the case of melanoma models, the medium survival time of the mice in the attenuated *Salmonella* VNPpadhEEnd group is 28.5 days, while that in the control group and the attenuated *Salmonella* VNP group is 11.5 days and 19.5 days respectively; in comparison with that of the control group, the medium survival time of the mice in the attenuated *Salmonella* VNPpadhEEnd group is significantly improved; the 30-day survival rate of mice in the attenuated *Salmonella* VNPpadhEEnd group and the attenuated *Salmonella* VNP group is 25% and 0% respectively.

In comparison with the prior methods of anaerobic-specific gene therapy that adopts anaerobic-specific promoter and anaerobic-targeted bacteria as the delivery system, the present invention has following beneficial effects:

(1) The present invention provides an anaerobic-specific adhE gene screened out from *Salmonella* VNP2009 through the proteomic technique; the expression level of the said anaerobic-specific adhE under anaerobic conditions is 120 times as much as that under aerobic conditions, therefore the padhE is a high-level, anaerobic-specific promoter. The in vivo experiment shows that the promoter padhE can initiate high-level, tumor-specific expression of target genes such as luciferase, GFP and Endostatin.

(2) The present invention not only realizes the anaerobic tissue (including tumor tissue) targeted delivery of the target gene by means of anaerobic-targeted bacteria, but also, due to the fact that the prokaryotic promoter padhE initiates the expression of the target gene only under hypoxic or anaerobic conditions, prevents expression of the target gene in other normal tissues, and consequently lowers down the potential in vivo toxicity of the target gene. The present invention realizes both the specific delivery of the target gene in the anaerobic tissue and the selective expression of the target gene in the anaerobic tissue; the said selective expression of the target gene takes place naturally in the core (therefore hypoxic or anaerobic) area of tumor tissue, requiring no extra artificial inductive measures.

(3) The present invention discovers that the low-copy plasmid can realize stable in vivo existence of the target gene so that a better therapeutic effect can be achieved.

(4) In most of the prior researches about tumor-targeted bacteria-induced gene therapy, though the target gene showed a certain degree of antitumor effect, its in vivo and in vitro expression levels were too low to be detected by such conventional methods as protein electrophoresis and western blot. In contrast, the method provided in the present invention, the anaerobic tissue-specific therapeutic gene initiated by the promoter padhE, can reach high level of expression, and therefore can be detected by such conventional methods as protein electrophoresis and western blot under both in vivo and in vitro conditions. Therefore, the present invention not only solves the technical difficulties appeared in specific delivery and selective expression of the target gene in the anaerobic tissue (including tumor tissue), but also realizes high-level expression of the target gene under both in vivo and in vitro conditions, including in the tumor tissue, which consequently guarantees a good therapeutic effect of the anti-anaerobic (including anti-tumor) medicine prepared with the method disclosed herein.

In conclusion, the present invention provides a method for screening the high-effective, anaerobic-specific promoter through the proteomic technique; with the promoter padhE prepared in this way, the present invention also provides a method for realizing specific delivery and stable expression of the padhE-initiated target gene in the anaerobic tissue, and the practical application thereof.

BRIEF DESCRIPTION

Description of Abbreviations

VNP: attenuated *Salmonella typhimurium* VNP20009; adhE: alcohol dehydrogenase gene; VNPpLuc: VNP bearing luciferase plasmid (without promoter); VNPpadhEEnd: VNP bearing pEndostatin plasmid; VNPpBR: VNP bearing pBR322 idle plasmid; mutVNP-GFP:VNP with GFP integrated into its genome; GFP: green fluorescence protein FIG. 1A. 2D electrophoresis images showing different expression of VNP under anaerobic and aerobic conditions. 1. anaerobic-induced expression; 2. aerobic culture.

Figure 1B:
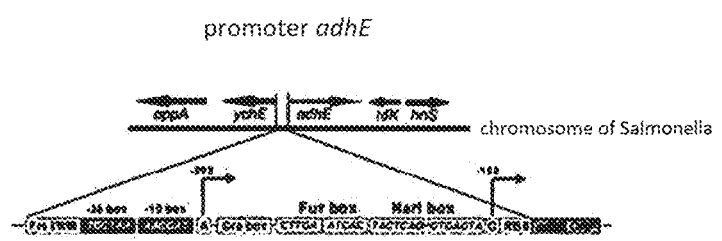

FIG. 1B. Structural representation of the promoter adhE determined out with mass spectrometry.

Analysis of alcohol dehydrogenase promoter initiating expression of GFP or promoting secretory expression of Endostatin under anaerobic conditions.

Figure 2A:
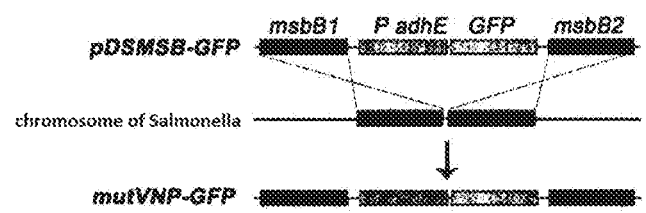

FIG. 2A. Method for constructing a strain with stable expression of GFP. AdhE-GFP fragment is homologously integrated into the chromosome of NVP. msbB1: msbB homology arm 1; PadhE: adhE promoter; GFP: green fluorescence protein; masbB2: msbB homology arm 2.

Figure 2B:
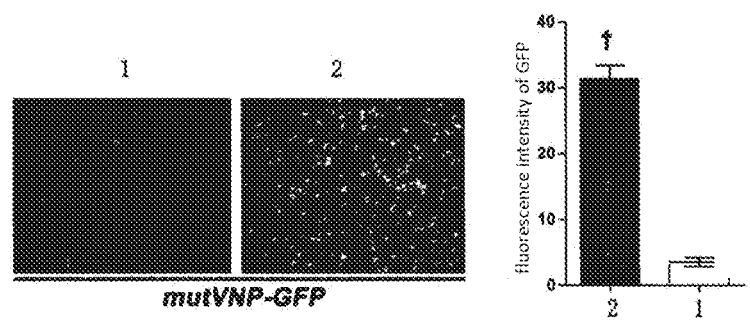

FIG. 2B. Analysis of anaerobic-induced expression and flow fluorescence quantitation of mutVNP-GFP with fluorescence microscopy. Fluorescence intensity is the mean value of different sample groups (mean standard deviation, n=3, †P<0.001)

Figure 2C:

FIG. 2C. The construction of the secretory expression vector of endostatin. PadhE: adhE promoter; SPA: secretion signal of Staphylococal protein A; Endostatin: endostatin gene.

Figure 2D:
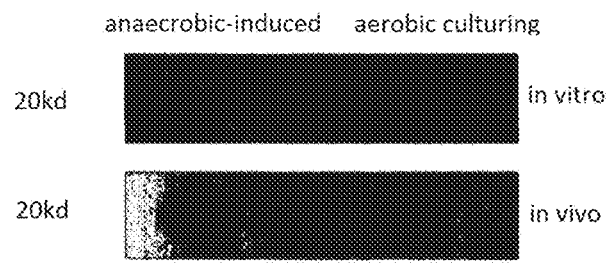

FIG. 2D. Western blot analysis of extracellular and intracellular endostatin expression of VNP bearing padhEEnd plasmid using anti-human endostatin antibody 1: anaerobic culture; 2: aerobic culture; 3:supernatant from extracellular culture; 4: supernatant after cell lysis.

Selective aggregation and tumor-targeted gene expression of *Salmonella typhimurium* VNP20009 in B16F10 melanoma.

Figure 3A:
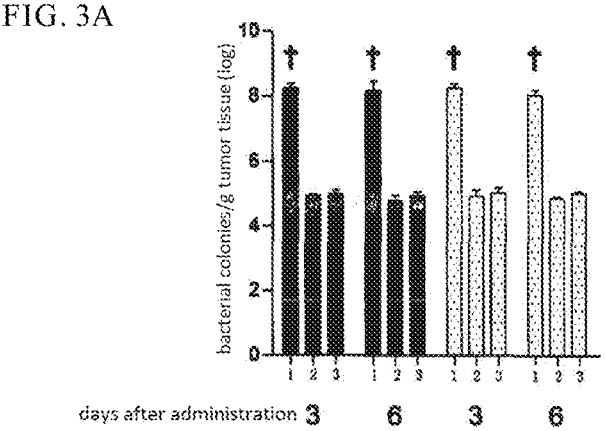

FIG. 3A. *Salmonella* VNP bearing luciferase plasmid and its induced expression. At different time points after administration, extracting animal tissues, rendering them into homogenates and determining luciferase values respectively (mean standard deviation, n=3, †P<0.001; in comparison with those in liver and spleen tissues, the luciferase value in tumor tissue is very high.). 1. tumor tissue; 2. liver tissue; 3. spleen tissue.

Figure 3B:
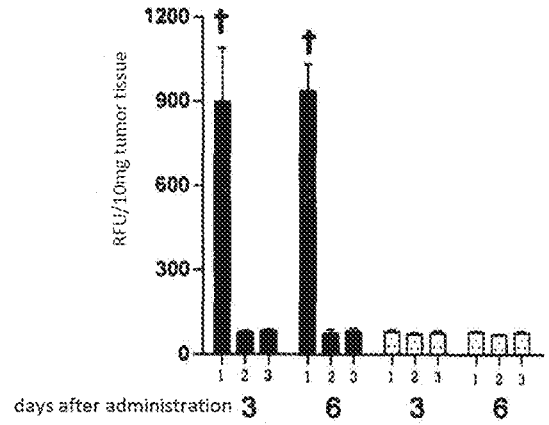

FIG. 3B. Analysis of adhE in C56BL/6 mice with the lucifrase reporter gene assay. (mean standard deviation, n=3, †P<0.001). 1. tumor tissue; 2. liver tissue; 3. spleen tissue.

Figure 3C:
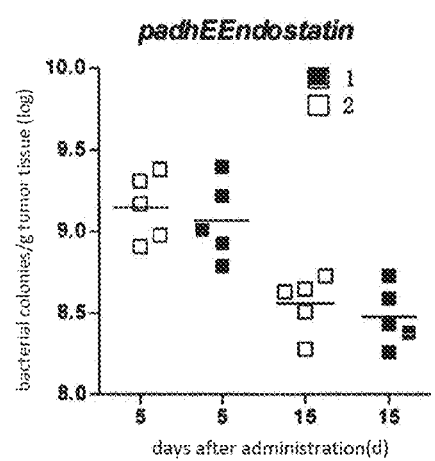

FIG. 3C. Analysis of the stability of padhEEnd plasmid carried by *Salmonella* in tumor. The total bacteria are counted on a LB plate without ampicillin resistance (indicated by blank boxes); the plasmid-containing bacteria is counted on a LB plate with ampicillin resistance (indicated by filled boxes). Each spot represents a mouse. 1. with ampicillin resistance; 2. without ampicillin resistance.

Figure 3D:
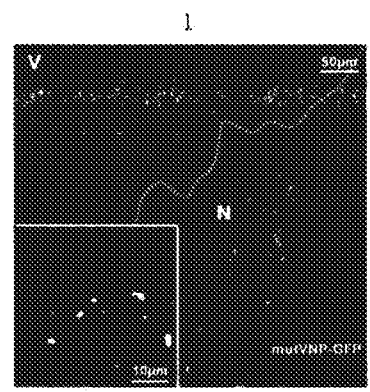

FIG. 3D. Confocal fluorescence microscopy verification of selective aggregation of *Salmonella* mutVNP-GFP in anaerobic and necrotic areas of the tumor; the promoter adhE can induce the gene expression in these areas. V: neoplastic cells; N: necrotic area 1. confocal fluorescence microscopy image of the tumor tissue infected with *Salmonella* mutVNP-GFP. All said experiments are conducted three times.

Verification of antitumor effect of *Salmonella* VNPpadhEEnd on mice models bearing Lewis lung cancer or melanoma.

Figure 4A:
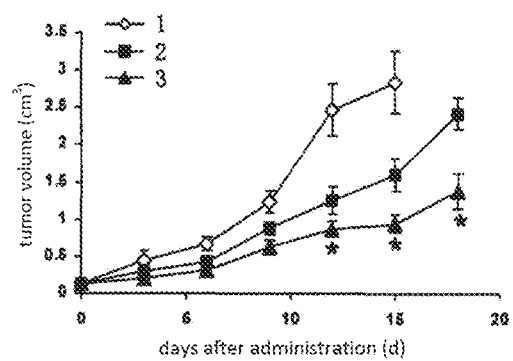

FIG. 4A. Average volume change of Lewis lung cancer in different groups, n=7 (n refers to the number of animals in each group). *P<0.05. 1. control group; 2. *Salmonella* VNP group; 3. *Salmonella* VNPpadhEEnd group.

Figure 4B:
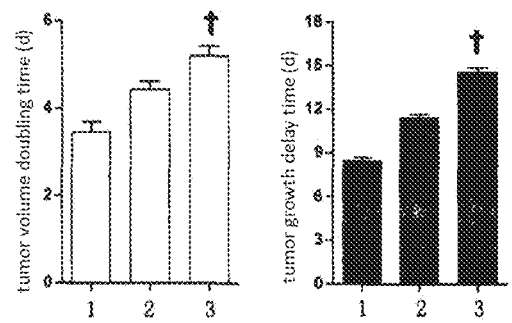

FIG. 4B. Analysis of the volume doubling time and growth delay time of Lewis lung cancer in different group. n=7. †p<0.001; very significant difference is shown between the *Salmonella* VNPpadhEEnd group and the *Salmonella* VNP group. 1. control group; 2. *Salmonella* VNP group; 3. *Salmonella* VNPpadhEEnd group.

FIG. 4C. Average volume change of B16F10 melanoma in different groups, n=8 (n refers to the number of animals in each group). *P<0.05. 1. control group; 2. Salmonella VNP group; 3. Salmonella VNPpadhEEnd group.

FIG. 4D. Analysis of the volume doubling time of B16F10 melanoma in each group. n=8. †p<0.001; very significant difference is shown between the Salmonella VNPpadhEEnd group and the Salmonella VNP group. 1. control group; 2. Salmonella VNP group; 3. Salmonella VNPpadhEEnd group FIG. 4E. Analysis of the growth delay time of B16F10 melanoma in each group. n=8. †p<0.001; very significant difference is shown between the Salmonella VNPpadhEEnd group and the Salmonella VNP group. 1. control group; 2. Salmonella VNP group; 3. Salmonella VNPpadhEEnd group.

Significant effect of Salmonella-induced padEEnd gene therapy in extending the survival time of mice bearing Lewis lung cancer or melanoma.

Figure 5A:
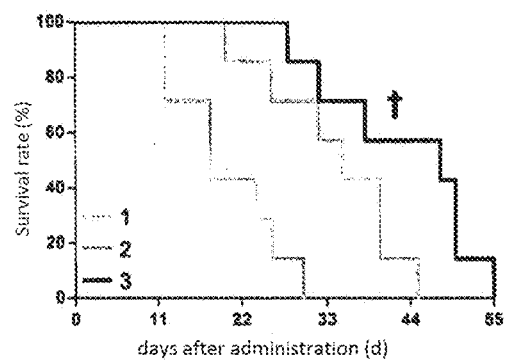

FIG. 5A. In comparison with the control group, Salmonella VNPpadhEEnd can significantly extend the survival time of mice bearing Lewis lung cancer. mean standard deviation, n=7, †P<0.001, the Kaplan-Meier survival analysis shows that very significant difference exists between the Salmonella VNPpadhEEnd group and the control group. 1. control group; 2. Salmonella VNP group; 3. Salmonella VNPpadhEEnd group.

Figure 5B:
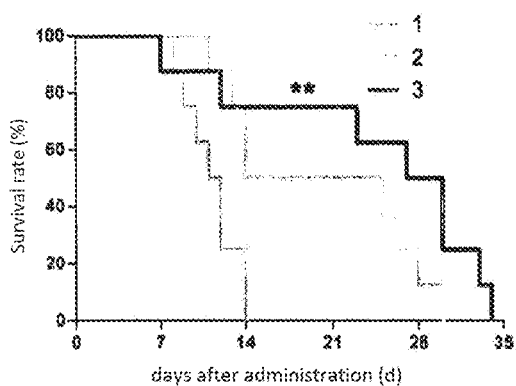

FIG. 5B. In comparison with the control group, Salmonella VNPpadhEEnd can significantly extend the survival time of mice bearing B16F10 melanoma. mean standard deviation, n=8, †P<0.01, the Kaplan-Meier survival analysis shows that very significant difference exists between the Salmonella VNPpadhEEnd group and the control group. 1. control group; 2. Salmonella VNP group; 3. Salmonella VNPpadhEEnd group.

FIG. 6 Significant effect of Salmonella VNPpadhEEnd in inhibiting tumor angiogenesis under both in vivo and in vitro conditions.

Figure 6A:
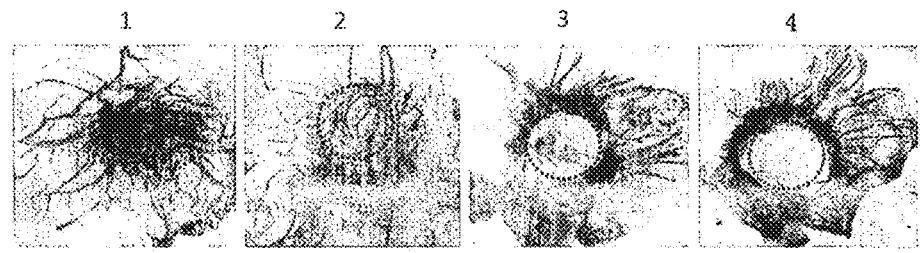

FIG. 6A. CAM (chick embryo chorioallantoic membrane assay) analysis. Inoculating the 8-day-old chicken embryos with differently modified bacteria; analyzing the inoculated areas of chorioallantoic membrane 48 hours after inoculation. 1. PBS control group; 2. Salmonella VNP supernatant group, dosage: 200 mg protein/embyo; 3. Salmonella VNPpadhEEnd supernatant group, dosage: 100 mg protein/embryo; 4. Salmonella VNPpadhEEnd supernatant group, dosage: 200 mg protein/embryo.

Figure 6B:
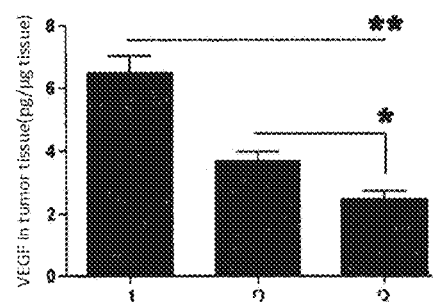

FIG. 6B. Analysis of VEGF level in tumor after treatment of Salmonella VNPpadhEEnd. 1. control group; 2. Salmonella VNP group; 3. Salmonella VNPpadhEEnd group. n=3, namely three mice in each group; *P<0.05 indicating that Salmonella VNPpadhEEnd strongly reduces the level of VEGF in the tumor in comparison with Salmonella VNP; **P<0.01 indicating Salmonella VNPpadhEEnd fairly strongly reduces the level of VEGF in the tumor in comparison with the control group.

Figure 6C:
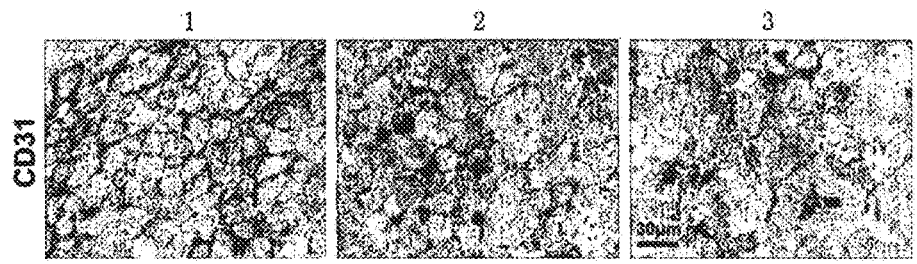

FIG. 6C. Tissue section analysis of tumor capillary after drug administration using CD31 staining (400 times magnification). 1. control group; 2. Salmonella VNP group; 3. Salmonella VNPpadhEEnd group.

Figure 6D:
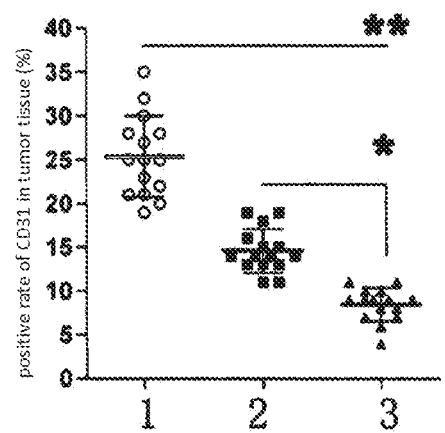

FIG. 6D. Quantitative analysis of CD 31 in tumor tissue. n=3, namely three mice in each group; *P<0.05 indicating that Salmonella VNPpadhEEnd strongly inhibits tumor angiogenesis characterized by CD31; **P<0.01 indicating Salmonella VNPpadhEEnd fairly strongly inhibits tumor angiogenesis (characterized by CD31) in comparison with the control group. 1. control group; 2. Salmonella VNP group; 3. Salmonella VNPpadhEEnd group.

Administration of Salmonella VNPpadhEEnd to induce necrosis and apoptosis of melanoma cells, and to promote colonization of the bacteria.

Figure 7A:
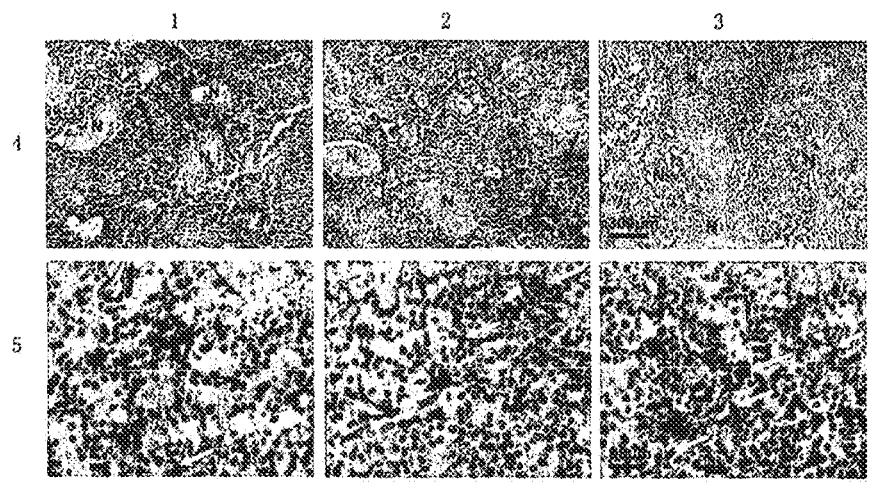

FIG. 7A. Tissue section analysis of necrosis and apoptosis in tumor tissue after administration of Salmonella VNPpadhEEnd. The necrosis of the tumor tissue is analyzed through HE staining (100 times magnification). The neoplastic cells are indicated by blue arrows. The apoptosis of tumor cells is analyzed through TUNEL Assay (200 times magnification). TUNEL positive cells are indicated by green arrows. 1. control group; 2. Salmonella VNP group; 3. Salmonella VNPpadhEEnd group; 4. HE stain analysis; 5. TUNEL Assay.

Figure 7B:
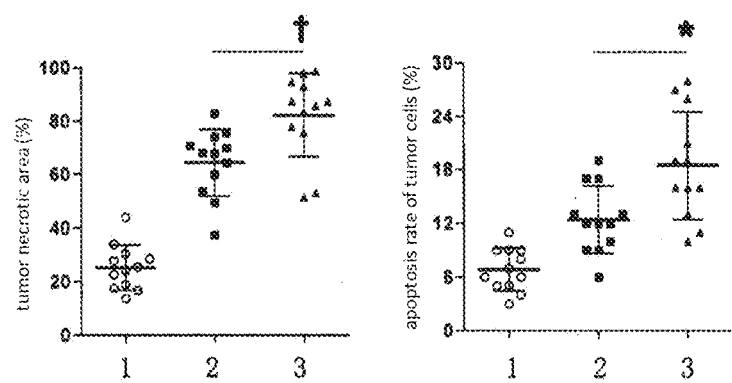

FIG. 7B. Quantitative analysis of necrosis and apoptosis in tumor. The quantitation of necrosis in tumor is conducted with the software Image J.; preparing 4 sections along different axes of the tumor from each mouse, four mice in each group. The TUNEL positive cells are counted at three areas where their density appears highest. †P<0.01 indicates the Salmonella VNPpadhEEnd group can very strongly induce tumor necrosis in comparison with the Salmonella VNP group. *P<0.05 indicates the Salmonella VNPpadhEEnd group can strongly induce tumor necrosis in comparison with the Salmonella VNP group.

Figure 7C:
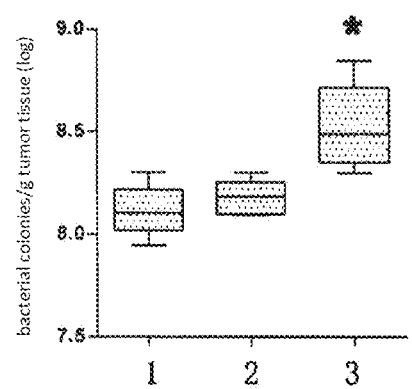

FIG. 7C. Titer analysis of bacteria in tumor 12 days after drug administration. n=4, namely four mice in each group, †P<0.05, the Salmonella VNPpadhEEndostatin group can strongly promote the colonization of bacteria in comparison with Salmonella VNPpBR group.

DETAILED DESCRIPTION

The present invention is more specifically described in the following paragraphs by examples.

TABLE 1 primers adopted for gene cloning and recombinant plasmid construction

| primers | nucleotide sequence | description |
| --- | --- | --- |
| AP-1 | gTATCTAgAGTTgAATCACggTTAgCT* | adhE upstream region, 5'-primer |
| AP-2 secretion | gTTTTTCTTTTTCAAAATgCTCTCCTgATAATg | adhE upstream region, 3'-primer |
| SPA-1 | TTGAAAAAGAAAAACATTTATTCAATTC | SPA secretory signal, 5'-primer |
| SPA-2 | gCATTTgCAgCAggTgTTAC | SPA secretory signal, 3'-primer |
| GFP-1 | TGCTGCAAATGCTATggTgAgCAAgggCgA | qfp gene, 5'-primer |

TABLE 1-continued primers adopted for gene cloning and recombinant plasmid construction

| primers | nucleotide sequence | description |
|---|---|---|
| GFP-2 | ATACTgCAgTTACTTgTACAgCTCgTCCA | gfp gene, 3'-primer |
| MSB-1 | gCgTCTAgAGTgAgCAgATCgTCCATTG | mutated msbB fragment, 5'-primer |
| MSB-2 | gAgCTgCAgCGTTACATGCACTTGCGTA | mutated msbB fragment, 3'-primer |
| LUC-1 | TGCTGCAAATGCTATGGAAGACGCCAAAAAC | luciferase gene, 5'-primer |
| LUC-2 | GACGTCGACTTACAATTTGGACTTTCCGCCCTT* | luciferase gene, 3'-primer |
| ENDO-1 | TgCTgCAAATTgCTCATAgCCACCgCgA | human endostatin gene, 5'-primer |
| ENDO-2 | gAggTCgACCTACTTggAggCAgTCATg⁺ | human endostatin gene, 3'-primer |

1. Construction of Expression Vectors

All the constructing enzymes and the plasmid pBR322 adopted herein were purchased from TAKARA company of Japan due to their excellent in vivo stability. The gene sequences of human endostatin and *Salmonella* adhE were cited from NCBI Database of the U.S.

Construction of Luciferase-Related Vectors:

(1) Construction of pLuc:

Adopting the primers Luc-3(5'-TCTAAGCTTATG-GAAGACGCCAAAAAC-3') and Luc-4 (5'-TATGTC-GACTTACACGGCGATC-3') to amplify luciferase gene from the plasmid pGL3-basic (Promega Company, U.S.), cleaving the sequence with endonucleases Hind III and Sal I, and then combining it with the vector pBR322 that has also been cleaved by Hind III and Sal I; transforming the product into TOP 10 competent cells, and after the clone culture and screening process, the clone so obtained bears no promoter and is used as luciferase control plasmid.

(2) Construction of padhELuc:

Adopting the Primers LUC-1(5'-TGCTGCAAATGC-TATGGAAGACGCCAAAAAC-3') and LUC-2 (5'-GACGTCGACTTACAATTTGGACTTTCCGCCCTT-3') to amplify luciferase gene from the plasmid pGL3-basic (Promega Company, U.S.); adopting the primers AP-1 (5'-GTAT CTAGAGTTGAATCACGGTTAGCT-3') and AP-2-secretion (5'-GTTTTTCTTTTTCAAAATGC TCTCCTGA-TAATG-3') to amplify adhE gene from *Salmonella* VNP20009 genome; and then ligating together the luciferase fragment and the promoter adhE fragment through overlapping PCR reaction; the product so obtained is then cleaved by Hind III and Sal I, and spliced together with the vector pBR322 that has also been cleaved by Hind III and Sal I; transforming the product into TOP 10 competent cells, and after the clone culture and screening process, the clone so obtained bears the promoter adhE and is used as luciferase expression plasmid.

(3) Construction of pDSMSB-GFP Suicide Vector:

Adopting the primers GFP-1(5'-TGCTGCAAATGC-TATggTgAgCAAGGGCgA-3') and GFP-2(5'-ATACTG CAGTTACTTGTACAGCTCGTCCA-3') to amplify GFP fragment from the plasmid pEGFP (Clontech Company, U.S.); adopting the said primers to amplify the promoter adhE gene, splicing it together with the adhE fragment again through overlapping PCR reaction, and then adopting the primers MSB-1(5'-GCGTCTAGAGTGAGC AGATCGTC-CATTG-3') and MSB-2 (5'-GAGCTGCAGCGTTACATG-CACTTGCGTA-3') to obtain MSB fragment from *Salmonella* genome through amplification; the said MSB fragment is a homologous recombinant fragment; the product is then cleaved by endonucleases Hind III and Sal I, and is combined together with pDS132 vector that has also been cleaved by Hind III and Sal I; transforming the product into TOP 10 competent cells, and after the clone culture and screening process, the clone so obtained is GFP suicide vector bearing the promoter adhE (4) Construction of Secretory Expression Plasmid of Endostatin Adopting the primers ENDO-1(5'-TGCTGCAAATGCT-CATAGCCACCGCGA-3') and ENDO-2 (5'-GAGGTC-GACCTACTTGGAGGCAGTCATG-3') to amplify human endostatin gene from the plasmid pET28a-Endostatin (preserved in the inventors' laboratory); adopting the primers SPA-1(5'-TTGAAAAAGAAAAACATTTATTCAATTC-3') and SPA-2(5'-GCATTTGCAGCAGG TGTTAC-3') to amplify SPA secretory signal fragment; and then adopting SPA-1 and SPA-2 again to ligate the said SPA secretory signal fragment together with the said human endostatin gene; adopting the primers AP-1 and ENDO-2 to splice the fragment so obtained together with the promoter adhE fragment through overlap PCR reaction; the product so obtained is cleaved by restriction endonucleases Hind III and Sal I, and is combined with the vector pBR322 that has also been cleaved by endonucleases; transforming the product into TOP10 competent state, and after clone culture and screening process, the clone so obtained is the secretory expression plasmid of endostatin bearing the promoter adhE.

2. Transfection of Recombinant *Salmonella*

Preparation of *Salmonella* competent cells before electrotransformation: keeping *Salmonella* VNP20009 in liquid LB culture medium at 37° C. till it reaches mid-exponential phase; collecting the bacteria with 6000 rpm centrifugation at 4° C., and washing the bacteria twice with sterile ultrapure water and 10% glycerol (both the sterile ultrapure water and the glycerol are cooled on ice in advance); and then diluting the concentration of the bacteria with 10% glycerol to $10^{10}$ cfu/40 μL 10% glycerol.

Electrotransformation of *Salmonella*: mixing the target gene plasmid with the said competent cells, placing the mixture on the ice for less than 5 min, then transporting the mixture into a 2 mm cuvette, fully removing the moisture outside of the cuvette and transforming the mixture with a gene pulser (Bio-Rad); the electrotransformation parameters are 1.6 KV, 25 μF and 400Ω; after the electrotransformation process, immediately sucking out the eletrotransformed bacteria, mixing them with 900 μL LB solution, and incubating in a shaking incubator for 1 hour at 37° C.; then centrifuging the solution at 4° C. and smearing the precipitate on ampicillin-resistant LB plate; keeping the plate at 37° C. for overnight incubation.

3. Analysis of the In Vivo Stability of the Recombinant *Salmonella* Bearing the pBR322 Vector Adopting the recombinant *Salmonella* bearing the common prokaryotic plasmid pBR322 (low-copy) to analyzing the loss of the plasmid in tumor-bearing mice, namely, the in vivo stability of the vectors; killing the tumor-bearing mice a certain period of time after drug administration, taking out the tumor tissue and making tissue homogenate in sterile PBS with a homogenizer [mass of tissue(g): volume of PBS(mL)=1:1]; sucking out the homogenate and gradiently diluting it with sterile PBS; then smearing the diluent on non-ampicillin-resistant and ampicillin-resistant LB plates respectively and keeping the plates at 37° C. for overnight incubation; analyzing the loss of the recombinant *Salmonella* plasmid on the ampicillin-resistant plate and the non-ampicillin-resistant plates respectively (only plasmid-containing recombinant *Salmonella* can grow on the ampicillin-resistant plate), and counting the bacterial colonies growing thereon.

4. 2D Electrophoresis and Mass Spectrometry Analysis (MALDI-TOF)

Separately culturing 10 mL *Salmonella* under aerobic and anaerobic conditions till they reach the density of $10^9$ cells/mL, harvesting the bacteria at 4° C. with centrifugation; then washing the bacteria with pre-cooled PBS three times and centrifuging the bacteria 5 min at 2000 g; resuspending the bacterial culture in a cell lysis solution (containing 7 M urea, 2 M sulfourea, 40 mM DTT, 2% IPG buffer), and then freeze-thawing the solution with liquid nitrogen three times; adopting ultrasonic treatment to remove the nucleic acid in the lysis solution, and then centrifuging the solution 60 min at 4000 g; determining the protein concentration in the supernatant after centrifugation with Bradford Assay. All steps mentioned above shall be conducted on the ice. The quantity of each sample is 120 µg total protein. Adopting on the gel strips (pH 3-10, linear) the isoelectric focusing on one dimension and SDS-PAGE separation on the other dimension; and visualizing the separated protein spots with silver stain; washing the gel strips twice with double-distilled water, and scanning each strip at 300 dpi; the images are edited with the software Adobe Photoshop, and then analyzed with the software Image Master Platinum (GE Healthcare). The protein spots up-regulated twice as large are regarded with statistical significance. The protein spots with differential expression are cut out and then undergone trypsin digestion.

MALDI samples are prepared in reference to the operating requirements of the MALDI apparatus. The mass spectrometric data are obtained from an Ultraflex II MALDI-TOF-TOF mass spectrometer with the software FlexControl 3.0; the mass range at 700-4000 Da is recorded in cation reflection mode with MALDI-TOF spectra, the cation-accelerating voltage is 25 kv; the mass-spectrum data are analyzed with the software FlexAnalysis 3.0; peak detection algorithm: SNAP; S/N limit: 3; quality factor limit: 50; the ion peak of trypsin self-digestion (trypsin_[108-115], MH+842.509, trypsin_[58-77], MH+2211.104) is used as internal reference; all substrate, self-digested trypsin fragments and predictable polluting ions (keratin) are removed; the peptide mass fingerprinting finally obtained is compared with sequences in NCBInr20101105 database (containing 101942 sequences) with the software Mascot (v2.3.02). The significance threshold of MOWSE scoring is set at $P<0.05$, lowest quality precision 120 ppm; as trypsin is a digestive enzyme, one error in cleavage sites is allowable; taking cysteine carbamidomethylation as fixed modification and methionine oxidation as varied modification.

5. Construction of *Salmonella* VNP Strain Keeping Stable Anaerobic-Specific Expression of GFP Gene by Means of Chromosome Integration Adopting the adhE-GFP fragment, with the assistance of MSB acquired from the suicide vector, to realize specific recombination with the MSB region of the *Salmonella* VNP, and then integrating it into the VNP chromosome under ampicillin resistance. PCR reaction is adopted to further verify that GFP gene has been integrated into the chromosome of the *Salmonella* VNP strain (mutVNP-GFP), and keeps stable, anaerobic-specific expression therein.

Quantitative determination of GFP expression: culturing *Salmonella* mutVNP-GFP under aerobic and anaerobic conditions respectively till they reach an OD600 of 0.4; collecting 1 mL precipitate after centrifugation; resuspending the precipitate in 0.5 mL icy PBS, centrifuging the solution again and sucking out the supernatant; then dissolving the precipitate so obtained in 4 µL deionized water, putting a few drops on clean slides and examining it with an fluorescence microscope; meanwhile, lysing the remaining bacteria with ultrasound and filtering the bacterial with 0.22 µm pore size membrane; analyzing the GFP expression at the absorption peak of 485 nm with a flow cytometer.

6. Analysis of Luciferase Expression in the Tissue.

Mixing the PBS solution with tumor tissue, spleen tissue and liver tissue separately at the ratio of 1:1, and rendering the mixture into homogenates with a homogenizer; lysing the three homogenates with the lysis solution (containing 50 mM Tris-HCl, pH 8.3, 4 mM DTT, 20% (v/v) glycerol, 2% (v/v) TritonX-100, 2 mg/mL lysozyme), then incubating them 10 min at 25° C.; centrifuging the homogenates 10 min at 12000 rpm, 4° C.; sucking out the supernatants and examining the luciferase activity in these supernatants with the luciferase activity assay kit (Promega Company); including the following steps: firstly, mixing 10 µL samples and 10 µL substrate (LAR) together and starting counting time simultaneously; 10 seconds later, adopting Lumat LB9507 luminometer (Berthold Company) to measure the fluorescence values of luciferase reaction (RLU).

7. Western Blot Analysis and ELISA Analysis (1) Preparation of anaerobic culture medium: bathing the newly prepared LB solution in boiling water for 15 min to remove most of the dissolved oxygen; then adopting the gas-coordinating boiling method by introducing nitrogen gas into the LB solution to remove the residual oxygen therein; adding 50 µL 0.05% sodium sulfide and 0.05% cysteine into the culture bottle to maintain its reducing environment; then immediately covering the anaerobic culture bottle with an anaerobic rubber stopper and sealing it tight with a metal vial crimper; after high-temperature, high-pressure sterilization, the low-oxygen, sterile LB culture medium is obtained.

(2) Western blot analysis: adopting western blot to analyze the secretory expression of human endostatin in VNP under either aerobic or anaerobic conditions. Resuspending the precipitate of the expressed protein in 100 nM Tris/HCL (pH 7.4) solution, and treating the solution so obtained on ice with ultrasound for 30 seconds; precipitating and condensing the supernatant of the expression protein with TCA; all samples finally obtained are analyzed with the standard western blot method. The rabbit anti-human endostatin antibody used in the analysis is purchased from Santa Cruz Company, U.S.

(3) ELISA analysis: dissolving the remaining tumor tissue with the extraction solvent (50 mM HEPES, pH 7.4, 100 mM NaCl, 50 mM NaF, 2 mM EDTA, 1% Triton-100 and 100 mg/mL PMSF) at the ratio of 1:8, putting it on ice for 1 hour; adopting Bradford Assay to analyze the protein concentration in the tissue; determining the VEGF concentration in the tumor with the ELISA kit made by Boster (Boshide) Company, China.

8. Analysis of CAM Assay

Filtering the lysed supernatant of expressed protein with the 0.22 μm pore size membrane to remove the bacteria; determining the protein concentration of the solution and adjusting the final concentration to 20 mg/mL; inactivating lipopolysaccharides (LPS) in samples with 10 μm/mL polymyxin B. All steps should be conducted under sterile conditions. Purchasing healthy 6-day-old chicken embryos and keeping them in a 37° C., 90% humidity environment; after two days' incubation, opening a small hole at the obtuse end of each embryo and putting a piece of Whatman filter paper on the chorioallantoic membrane, and then administering the drug through the filter paper; continuing to incubate the embryos for another 48 hours, fixating the filter paper on the chorioallantoic membrane and taking them out for photographing.

9. Tumor Planting and Assessment of Antitumor Effect.

Dissolving melanoma B16F10 cells and Lewis lung cancer cells separately into PBS solution, counting the cells and keeping the final concentration of tumor cells at $5\times10^5$ cells/0.1 mL or $10^6$ cells/0.1 mL PBS; hypodermically injecting C57BL/6 mice with 0.1 mL of tumor cells so prepared at the right side under the armpit;

Administration plan of recombinant *Salmonella*: the tumor is visible 7 days after the establishment of tumor models; its volume is about 0.3 cm$^3$; centrifuging the plasmid-bearing *Salmonella* and washing the bacteria with sterile PBS, injecting each mouse with $10^5$ cfu bacteria through abdominal injection.

The antitumor effect of the recombinant *Salmonella* is assessed with reference to related literature; the tumor volume is calculated according to the following formula: tumor volume=length×width$^2$×052; meanwhile, the survival rate of mice is recorded. Another two parameters, the tumor volume doubling time and tumor growth delay time, are adopted in the assessment; the tumor volume doubling time refers to the time a tumor takes to double its volume while the tumor growth delay time refers to the time a tumor takes to reach the volume of 1000 mm$^3$. All animal experiments are conducted in the animal laboratory of Nanjing University, with related regulations well observed.

10. Tissue Section Analysis (1) HE stain analysis: taking out the tumor tissue and fixating it with 4% formaldehyde overnight; then sequentially treating the tissue with paraffin embedding, sectioning and dewaxing; after standard procedures of HE stain, analyzing the tumor tissue with a microscope.

(2) Analysis of tissue sections with CD31 staining: CD31 is a molecular marker widely used to characterize vascular endothelial cells formed in angiogenesis. Taking out the tumor tissue from the treatment groups (with endostatin gene therapy) and the control group respectively, fixating it with 4% formaldehyde overnight; then sequentially treating the tissue with paraffin embedding, sectioning and dewaxing; then retrieving the antigen with high-temperature, high-pressure sodium citrate solution; adopting goat anti-mouse CD31 antibody (Santa Cruz Company, U.S.) for primary antibody incubation (1:2000, 4° C., overnight), washing the slides with PBST three times, 5 minutes each time; and then incubating with the secondary antibody (1:200; 1 hour); washing the slides with PBST three times and dyeing the slides with DAB; when the color turns physically visible, stopping dyeing process with distilled water and rinsing the slides with clean water; then adopting haematoxylin to redye the nucleus; drying the slides and mounting them with dry gum; analyzing the sections with a microscope. The quantitative analysis of CD 31 is conducted with reference to the method disclosed in the cited document [Jia L J, et, al. 2007, International Journal of Cancer 121:666-674].

(3) TUNEL analysis of tumor tissue sections: taking out the tumor tissue in mice and preparing 5 μm frozen sections; adopting the TUNEL kit (Boster Company, China) to analyze apoptosis of cells. The specific procedure is conducted in accordance with operating instructions of the kit.

The present invention adopts the proteomic technique to screen out anaerobic-specific gene and its promoter; the said promoter of the target gene is anaerobic-specific, therefore it can initiate the expression of the target gene under hypoxic or anaerobic conditions. The said proteomic technique for screening the anaerobic-specific bacterial gene and its promoter is further adopted to screen out the anaerobic-specific adhE from *Salmonella*; the expression level of the said anaerobic-specific adhE under anaerobic conditions is 120 times as much as that under aerobic conditions (FIG. 1A).

The said promoter padhE is highly conservative in pro-karyotic cells. Its DNA sequence has 100% identity with the DNA sequence of such serotypes of *Salmonella enterica* as *S. typhimurium* 4/74, T000240, SL1344, 14028S, D23580, LT2, *S. Heidelberg* SL476, etc.; 99% identity with the DNA sequence of such serotypes of *Salmonella enterica* as *S. enteritidis* P125109, *S. dublin* CT_02021853, *S. gallinarum.* 287/91, *S. newport* SL254, and *S. paratyphi* SPB7, etc.; 98% identity with the DNA sequence of such serotypes of *Salmonella enterica* as *S. agona* SL483, *S. schwarzengrund* CVM19633, *S. choleraesuis* SC-B67, *S. paratyphi-C* RKS4594, *S. typhi* Ty2, *S. weltevreden* 2007-60-3289-1, *S. paratyphi-A* AKU 12601 and *S. paratyphi-A* ATCC 9150, etc.; 98% identity with the DNA sequence of *S. typhi* CT18; 93% identity with the DNA sequence of such serotypes of *Salmonella enterica* as *S. arizona* 62:z4 and z23:--; 88% identity with the DNA sequence of *Klebsiella variicola* At-22 and such serotypes of *Klebsiella pneumoniae* as NTUH-K2044, 243, MGF78578; 81% identity with the DNA sequence of *Citrobacter koseri* ATCC BAA-895; 80% identity with the DNA sequence of *citrobacter rodentium* ICC168; 79% identity with the DNA sequence of *Shigella dysenteriae* Sd197; 77% identity with the DNA sequence of such serotypes of *E. coli* as SMs-3-5, 536, 083: H1, UM146, IHE3034, 026:H11, LF82, S88, APEC 01, UTI89, KO11, W, BL21(DE3), ETEC H10407, ABU83972, O111: H-strain, 0103: H2, *E. coli* B REL606, BL21-Gold(DE3)pLysS AG', UMN026, ED1a, IAI39, IAII, 55989, SE11, ATCC8739, E24377A, HS, CFT073, 042, DH1(ME8569), DH1, 0157: H7, BW2952, 0127:H6E2348/69, 0157: H7 EC4115, K12 DH10B, K12 W3110, K12 MG1655, 0157:H7-0157: H7EDL933, 0155:H7-CB9615 and SEI5; 77% identity with the DNA sequence of *Escherichia fergusonii* ATCC 35469; 77% identity with the DNA sequence of such serotypes of *Shigella dysenteriae* as 2002017, 2a and 2a 2457T; 77% identity with the DNA sequence of *Shigella sonnei* SS046, *Shigella boydit* CDC3083-94, *Shigella flexneri* 5-8401 and *Shigella boydit* Sb227; 76% identity with of the DNA sequence of *E. coli* 0157; and 75% identity with the DNA sequence of *enterobacter cloacae* SCF1. As shown above, the said promoter padhE is highly conservative in bacteria, and all padhE promoters made from prokaryotic bacteria can be used to initiate anaerobic-specific expression of the bacteria-induced target gene.

In addition, the core sequence of said promoter padhE must contain the sequences at least 1200 bp upstream from the adhE gene so that this promotor can initiate the selective expression under hypoxic or anaerobic conditions. Within the said sequence, the sequences at 500 bp and 1000 bp upstream of the adhE gene can also realize high-level expression of the reporter gene, however, both of them are not anaerobic-specific; on the contrary, the DNA sequence at 1000 bp-1200 bp upstream of the adhE gene can guarantee high-level anaerobic expression of the said promoter. As to the sequence extending further than 1200 bp upstream of the adhE gene, it certainly has selective expression property due to the fact that such a sequence contains the DNA sequence at 1200 bp upstream of the adhE gene; the region around 1200 bp contains a part of ychE gene that is further upstream of the adhE gene, the said ychE gene is of assistance to the promoter padhE In order to prove that the promoter padhE screened out with the method provided in the present invention can successfully initiate the target gene into anaerobic-specific expression, the present invention adopts gene fragments from difference sources, including human endostatin (C-terminal fragment of collagen XVIII), green fluorescence protein (GFP) from the jellyfish, and firefly luciferase gene from the insect, to construct different padhE-bearing expression vectors. All of the expression vectors from different sources can realize high-level in vitro expression in anaerobic-target bacteria under hypoxic or anaerobic conditions (FIGS. 2A, 2B, 2C, and 2D); they can also reach selective in vivo expression in anaerobic tumor tissue (FIG. 3A, 3B, 3D) and no expression in other normal tissues (FIG. 2B, 3B). In the in vitro experiments, the anoxic environment guarantees stable, specific expression of the promoter padhE carried by *Salmonella* (FIG. 2B, 2E); the analysis of in vivo expression of luciferase and endostatin genes also indicates that the target gene carried by bacteria does show such properties as targeted delivery to the anaerobic tissue and selective expression in the tumor tissue. The in vivo expression level of all exogenous genes initiated by padhE is easily to be detected out by means of a variety of testing methods, for example, activity assay of expressed product luciferase (FIG. 3B), fluorescence property assay of expressed product GFP (FIG. 2B); and western blot assay (FIG. 2D). The exogenous genes detected by different methods, despite different properties of their expressed products, share one common point, namely, all assays prove the apparent, massive existence of expressed products. On the contrary, the expressed products in all prior cases of tumor-targeted bacteria-induced gene therapy are difficult to be detected, no matter under in vitro or in vivo conditions.

In order to precisely reflect the activity of the promoter adhE, the present invention integrates the single-copy adhE-GFP gene into the chromosome of *Salmonella* by means of homologous recombination so that the said gene can express GFP protein under anaerobic conditions. The results of all experiments show that only under anaerobic conditions can the GFP protein be highly expressed by *Salmonella*. The results also prove that only under anaerobic conditions can the promoter adhE exert its biological activity; it does not exert any biological activity under normal aerobic conditions (FIG. 2A, 2B). In the present invention, the inventors inserted a secretory signal peptide of SPA into the sequence upstream of the endostatin gene. The result of western blotting showed that 20 kDa endostatin protein was effectively expressed under anarobic condition, and then was secreted out of cells; this result could not be detected out under aerobic conditions.

Abdominally injecting *Salmonella* VNP20009 bearing padhELuc or pLuc plasmid into mice with B16F10 melanoma, analyzing bacterial colonies in the tumor, spleen and liver 3 days after injection; the results show that *Salmonella* VNP bearing padhELuc or pLuc plasmid proliferates enormously in the tumor, 1000 times as much as in other normal organs (FIG. 3A). Analyzing luciferase activity in tumor, liver and spleen 3 and 6 days after injection, the results show that the luciferase activity can be easily detected in the anaerobic tumor but cannot be detected in aerobic spleen or liver (FIG. 3B). More importantly, due to the anaerobic-specific expression of the promoter adhE, the high-level expression of VNPpadhELuc in tumor tissue causes no significant toxicity to liver or spleen (and among other normal organs, liver and spleen have the highest aggregation of VNP20009); this indicates that bacteria-induced adhE gene therapy is safe in the body.

Analyzing the growth of bacteria in tumor-bearing mice 5 and 15 days after abdominal injection, the results show that the growth of *Salmonella* VNP20009 bearing low-copy padhELuc or pLuc plasmid is very good, having as many colonies of bacteria as *Salmonella* bearing no plasmid; this indicates that the low-copy padhELuc plasmid does not interfere with the growth and proliferation of bacteria, and its stability in *Salmonella* can be maintained at least for 15 days (FIG. 3C). On the contrary, the expression vector originated from the high-copy pUC plasmid will significantly interfere with the growth and stability of the *Salmonella* VNP20009; the colonies of *Salmonella* VNP2000 will decrease accordingly as well. The analysis of fluorescence microscopy proves that the *Salmonella* bearing mutVNP-GFP aggregates in the anaerobic area of the tumor (FIG. 3D). The experiments mentioned above also prove that the bearing of adhE-initiated target gene does not change the anaerobic (tumor)-targeted property of *Salmonella* VNP20009.

In the present invention, the inventors also investigate the influence of plasmids with different copy numbers on the in vivo stability of the bacteria. The results show that the titer of the bacteria with low-copy pBR322 plasmid in the anaerobic tumor tissue is much higher than that of the bacteria with high-copy pUC18 plasmid. The titer ratio between them is about 1000:1. Therefore, the low-copy pBR322 plasmid is a better vector for gene therapy of tumors. The bacterial strain bearing pBR322 plasmid vector can keep a stable, high-titered in vivo existence in the anaerobic tumor tissue while the high-copy pUC18 may be a big metabolic burden for bacteria and results in the latter's unstable existence.

The present invention adopts a low-copy pBR322 plasmid as the expression vector. This vector presents very high in vivo stability. Experiments show that no significant loss of plasmid is found in the tumor tissue. The data of the present invention also indicate that the gene therapy conducted with this expression vector and the promoter padhE does not interfere with the tumor-targeted property of the bacteria and the distribution of bacteria in the tumor and other normal organs. The fact that the low-copy pBR322 plasmid is a better vector for gene therapy of tumors is firstly discovered by the present invention, in view of the fact that all other researchers and/or inventors are adopting the high-copy pUC18 plasmid as the expression vector at present. Most of the expression vectors in the present invention are constructed on the pBR322 plasmid. That's why the present invention can realize high-effective and stable expression of the exogenous genes, particularly the high-effective and stable in vivo expression.

In view of the fact that *Salmonella* VNP20009 predominantly aggregates in the anaerobic area of the tumor and the fact that the promoter adhE can initiate the selective expression in the anaerobic area of the tumor, the influence of *Salmonella* VNPpadEEnd upon the growth of the tumor in tumor-bearing mice is analyzed in the present invention. Firstly, in the case of treatment of Lewis lung cancer. Inoculating the mice bearing Lewis lung cancer with *Salmonella* VNPpadhEEnd and *Salmonella* VNP respectively; the results show that both *Salmonella* VNPpadhEEnd and *Salmonella* VNP can significantly reduce the growth speed of the tumor (P<0.01) in comparison with the control group; 12 to 18 days after inoculation, the volume of the tumor treated with *Salmonella* VNPpadhEEnd is significantly smaller than that treated with *Salmonella* VNP (P<0.05) (FIG. 4A); the analysis of the volume doubling time shows that the volume doubling time of the control group is 3.46 days (CI, 3.23-2.68 days), of *Salmonella* VNP group 4.44 days (CI, 4.27-4.61 days), of *Salmonella* VNPpadhEEnd group 5.21 days (CI, 4.99-5.42 days) (FIG. 4C, Table 2); the growth delay time of both the *Salmonella* VNP group (8.45 days) and *Salmonella* VNPpadhEEnd group (11.43 days) is significantly improved in comparison with the control group (11.43 days) (P<0.0001) (FIG. 4B, Table 2). Secondly, in the case of treatment of melanoma. The results show that the *Salmonella* VNPpadhEEnd group can significantly inhibit the growth of melanoma in comparison with the *Salmonella* VNP group and the control group (FIG. 4C); the volume doubling time of the *Salmonella* VNPpadhEEnd group (6.96 days; CI, 6.86-7.07 days) is significantly longer than that of the *Salmonella* VNP group (5.86 days CI, 5.70-5.98 days) and that of the control group (2.96 days, CI, 2.85-3.08 days) (P<0.001) (FIG. 4D, Table 2); meanwhile, the tumor growth delay time of the *Salmonella* VNPpadhEEnd group increases significantly, reaching 17.07 days in average, while the tumor growth delay time of the *Salmonella* VNP group and the control group is 12.90 days and 7.56 days respectively; in comparison with the *Salmonella* VNP group and the control group, the *Salmonella* VNPpadhEEnd group shows great statistic significance (P<0.001) (FIG. 4D, Table 2).

The present invention also investigates the survival time of the mice bearing Lewis lung cancer or melanoma undergoing the targeted treatment with *Salmonella*-induced endostatin. In the case of lung cancer models, the medium survival time of the mice in the *Salmonella* VNPpadhEEnd group is 49.0 days, significantly longer than that in the control group (18.0 days) and the *Salmonella* VNP group (25.92 days); the Kaplan-Meier survival analysis shows that the treatment with *Salmonella* VNPpadhEEnd can significantly improve the survival rate of mice (P<0.001); the 30-day survival rate of mice in the *Salmonella* VNPpadhEEnd group and the *Salmonella* VNP group is 86% and 71% respectively. In the case of melanoma models, the medium survival time of the mice in the *Salmonella* VNPpadhEEnd group is 28.5 days, while that in the control group and the *Salmonella* VNP group is 11.5 days and 19.5 days respectively; in comparison with that of the control group, the medium survival time of the mice in the *Salmonella* VNPpadhEEnd group is significantly improved (P<0.01); the 30-day survival rate of mice in the *Salmonella* VNPpadhEEnd group and the *Salmonella* VNP group is 25% and 0% respectively (FIG. 5A, 5B).

*Salmonella* VNPpadhEEnd can inhibit angiogenesis no matter under in vivo or in vitro conditions. In order to investigate whether endostatin expressed by *Salmonella* VNPpadhEEnd can inhibit angiogenesis under in vivo conditions, the CAM assay is conducted on 8-day-old chick embryos in the present invention. As shown in FIG. 6A, after the *Salmonella* VNPpadhEEnd treatment, an avascular area is left on the chorioallantoic membrane where the filter paper is located, which indicates that *Salmonella* VNP20009 does have the function to inhibit in vivo angiogenesis. On the basis of this experiment, the inventors of the present invention speculate that *Salmonella* VNP20009 may also inhibit angiogenesis in the tumor. After testing the expression of VEGF with ELISA Assay, they find that the *Salmonella* VNPpahEEnd group can significantly inhibit the expression of VEGF in comparison with the control group and the *Salmonella* VNP group (FIG. 6B). The immunohistochemical test show that the *Salmonella* VNPpadhEEnd group can significantly inhibit the expression of CD31 in comparison with the control group (FIG. 6C, 6D). All these experiments indicate that *Salmonella* VNPpadhEEnd can slow down the growth of the tumor through inhibiting angiogenesis in the tumor, which consequently improves the survival rate of melanoma-bearing mice.

The present invention also investigates the relationship between *Salmonella* VNPpadhEEnd treatment and tumor necrosis or apoptosis of tumor cells. The results indicate that the tumor tissue of the mice in the *Salmonella* VNPpadhEEnd group experiences more severe necrosis than that in the control group and the *Salmonella* VNP group. In the case of the *Salmonella* VNP group and the control group, the neoplastic cells and interspersed necrotic tissue coexist simultaneously, in contrast, *Salmonella* VNPpadhEEnd can induce expansive, continual necrosis in the tumor tissue. TUNEL Assay shows that more cells are undergoing apoptosis in the *Salmonella* VNPpadhEEnd group than that in the other groups. Therefore, *Salmonella* VNPpadhEEnd can inhibit the growth of B16F10 melanoma cells by inducing them into apoptosis (FIG. 7A, 7B). Further analysis shows that *Salmonella* VNPpadhEEnd can colonize in the tumor, and the anaerobic or necrotic environment can attract more *Salmonella* VNPpadhEEnd to colonize or proliferate therein (FIG. 7C). As the inhibition of angiogenesis will further increase the anaerobic areas in the tumor, a favorable situation for the bacteria to colonize or proliferate in the tumor, the antitumor effect of *Salmonella* VNPpadhEEnd is further enhanced. This is why the adoption of endostatin in inhibiting the angiogenesis can further improve the aggregation of bacteria in the tumor. This conclusion is consistent with the previous report conducted by the inventors of the present invention [Jia L J, et, al. 2007, International Journal of Cancer 121:666-674].

TABLE 2 growth curve, Kaplan-Meier survival analysis, and medium survival time in different groups

| | groups | n | growth curve$^a$ v(d) | r | tumor volume doubling time (d)$^b$ | tumor growth delay time (d)$^c$ | medium survival time | 30-day survival rate |
|---|---|---|---|---|---|---|---|---|
| Lewis | control | 7 | In(v) = 0.2009 d-1.69 | 0.9509 | 3.46(3.23-3.68) | 8.45(8.27-8.64) | 18.0(13.59-26.41) | 0.00 |
| | VNP | 7 | In(v) = 0.1583 d-1.81 | 0.9733 | 4.44(4.27-4.61) | 11.43(11.22-11.64) | 35.0(25.92-42.08)** | 0.71 |
| | VNPpadhEEnd | 7 | In(v) = 0.1341 d-1.95 | 0.9652 | 5.21(4.99-5.42)$^\dagger$ | 14.54(14.22-14.86)$^\dagger$ | 49.0(33.46-52.54)$^\dagger$ | 0.86 |
| B16SF10 | control | 8 | In(v) = 0.2342 d-1.77 | 0.9814 | 2.96(2.85-3.08) | 7.56(7.48-7.64) | 11.5(9.42-13.08) | 0.00 |
| | VNP | 8 | In(v) = 0.1186 d-1.53 | 0.9586 | 5.84(5.70-5.98) | 12.90(12.67-13.05) | 19.5(13.60-26.65)** | 0.00 |
| | VNPpadhEEnd | 8 | In(v) = 0.0996 d-1.70 | 0.9833 | 6.96(6.86-7.07)$^\dagger$ | 17.07(16.97-17.17)$^\dagger$ | 28.5(16.18-32.82)** | 0.25 |

All data listed herein are average values calculated at a 95% confidence interval (indicated in parentheses).
$^a$The growth curve shows the change of the tumor volume (V, cm$^3$) correlated to the growth days (d, days); r refers to the correlation coefficient.
$^b$The tumor volume doubling time is calculated in relation to the exponential function of the growth curve.
$^c$The tumor growth delay time refers to the time a tumor takes to reach the volume of 1000 mm$^3$ (mean standard deviation,
$^\dagger$P < 0.0001; the tumor growth delay time of the *Salmonella* VNPpadhEEnd is very significant in comparison with the *Salmonella* VNP group,
**P < 0.01). The medium survival time is calculated with the Software MedCalc; the figures in paratheses indicate the 95% confidence interval).

During the research phase of the present invention, the inventors attempted a variety of routes to deliver the bacteria bearing anaerobic-targeted bacteria-induced therapeutic gene to the body, including abdominal injection, intravenous injection and oral administration [Jia L J, et, al. 2007, International Journal of Cancer 121:666-674; Jia L J et, al. 2007, Cancer Science 98:1107-1112, 2007; Chen G, et, al. 2009, Cancer Science 100:2437-2443]. As shown in these researches, all administration routes can successfully deliver the bacterial strain modified by the padh-containing target gene to the body and can ensure its good antitumor effect; however, comparatively, the oral administration can not only effectively deliver the strain modified by the padh-initiated target gene to the body and realize the strain's targeted aggregation in the anaerobic tissue, but also greatly lower down the toxic and side effects of the bacterial strain.

While the objects, technical solutions and beneficial effects of the present invention have been described in the above embodiments, a person skilled in the art will recognize that these embodiments are only preferred examples of the present invention, not to limit the scope of the invention. Any modification, equivalent replacement, or improvement made without departing from the spirit and principle of the present invention should fall within the scope of the present invention.

The claims are as follows:

1. A method for initiating anaerobic-targeted delivery and stable, selective expression, comprising:
   providing an endostatin gene;
   isolating a high-effective, anaerobic-specific promoter that initiates anaerobic-specific expression, wherein the high-effective, anaerobic-specific promoter is an alcohol dehydrogenase promoter (padhE), further wherein the padhE promotor contains an active region that initiates anaerobic-specific expression, the active region starting at 500 bp upstream of a target gene of the anaerobic-specific promoter, and the padhE promotor also contains a regulatory region for anaerobic-specific expression starting at 1000 bp-1200 bp upstream of the target gene of the anaerobic-specific promotor;
   ligating the high-effective, anaerobic-specific promoter together with the endostatin gene, and combining the ligated product into a secretory expression plasmid;
   transforming the secretory expression plasmid into attenuated prokaryotic cells, wherein the attenuated prokaryotic cells are *Salmonella* cells;
   administering the attenuated prokaryotic cells for treatment of a tumor, wherein the tumor is one of Lewis lung cancer and melanoma, further wherein administration results in anaerobic-targeted delivery and stable, selective expression of the endostatin gene.

2. The method of claim 1, further wherein the regulatory region for anaerobic-specific expression contains a part of a ychE gene.

3. The method of claim 1, wherein administering the attenuated prokaryotic cells for treatment of a tumor is accomplished by one of abdominal injection, intravenous injection, and oral administration.

4. The method of claim 1, wherein administering the attenuated prokaryotic cells for treatment of a tumor includes administering for the treatment of a disease causing anaerobic tissues.

5. The method of claim 1, wherein the method for initiating anaerobic-targeted delivery and stable, selective expression of a target gene ensures that in vivo or in vitro expression of the target gene is only initiated under hypoxic or anaerobic conditions.

6. A method of gene therapy, comprising:
   preparing a bacterial strain, the bacterial strain being a *Salmonella* strain, wherein the bacterial strain is modified by a target endostatin gene initiated by a promoter padhE, wherein the promotor padhE contains a regulatory region for anaerobic-specific expression starting at 1000 bp-1200 bp upstream of the target gene, further wherein preparing the bacterial strain is accomplished by transforming a plasmid vector cloned with the target endostatin gene initiated by the promoter padhE into an anaerobic-targeted bacteria; and
   integrating the target endostatin gene initiated by the promoter padhE into a chromosome of the anaerobic-targeted bacteria;
   administering the bacterial strain modified by the target endostatin gene initiated by the promoter padhE for the treatment of a condition, wherein the condition is one of Lewis lung cancer and melanoma.

7. The method of claim 6, wherein administering the bacterial strain modified by the target endostatin gene initiated by the promoter padhE for the treatment of a condition is accomplished by one of abdominal injection, intravenous injection, and oral administration.

8. The method of claim 6, wherein the method of gene therapy ensures that in vivo or in vitro expression of the target endostatin gene is only initiated under hypoxic or anaerobic conditions.

9. The method of claim 6, further wherein the regulatory region for anaerobic-specific expression contains a part of a ychE gene.

* * * * *